United States Patent [19]

Reh et al.

[11] Patent Number: 4,695,656
[45] Date of Patent: Sep. 22, 1987

[54] PROCESS FOR THE PREPARATION OF 2,4-DINITROPHENYL ETHERS

[75] Inventors: Kuno Reh; Friedrich Schophoff, both of Frankfurt am Main, Fed. Rep. of Germany

[73] Assignee: Cassella Aktiengesellschaft, Frankfurt am Main, Fed. Rep. of Germany

[21] Appl. No.: 846,011

[22] Filed: Mar. 31, 1986

[30] Foreign Application Priority Data

Apr. 27, 1985 [DE]  Fed. Rep. of Germany ....... 3515339

[51] Int. Cl.[4] ................... C07C 43/025; C07D 307/02
[52] U.S. Cl. .................................... 568/587; 549/491; 568/586
[58] Field of Search ............... 568/711, 583, 584, 586, 568/587; 549/491

[56] References Cited

U.S. PATENT DOCUMENTS 2,048,172  7/1936  Wesson .............................. 568/584
2,988,571  6/1961  MacFie et al. .................. 568/586 X

OTHER PUBLICATIONS

Blanksma et al, Rec. Trav. Chim. 65 (1946) 711 & 715.
Authors: John A. Riddick and Emory E. Toops, Jr., "Organic Solvents", 1955 pp. 43, 44, 93, 116, vol. VII of *Technique of Organic Chemistry*.

*Primary Examiner*—J. E. Evans
*Attorney, Agent, or Firm*—Connolly and Hutz

[57] ABSTRACT

2,4-Dinitrophenyl ethers are prepared by reacting a 2,4-dinitrochlorobenzene or 2,4-dinitrobromobenzene with an alkali metal alcoholate in a non-polar, inert solvent, at a temperature from $-25°$ C. to $50°$ C.

12 Claims, No Drawings

PROCESS FOR THE PREPARATION OF 2,4-DINITROPHENYL ETHERS

The invention relates to a process for the preparation of 2,4-dinitrophenyl ethers of the general formula I

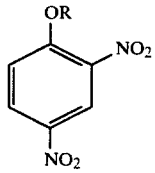 (I)

R denoting $(C_1-C_4)$alkoxy-$(C_2-C_4)$alkyl, phenoxy-$(C_2-C_4)$alkyl, $(C_1-C_4)$alkoxy-$(C_2-C_4)$alkoxy-$(C_2-C_4)$alkyl or tetrahydrofurfuryl.

The compounds of the formula I are important precursors, for example for the preparation of disperse dyes as are described in, for example, Belgian Pat. No. 634,032 (corresponding to U.S. Pat. No. 3,250,763).

Examples of suitable starting materials for the preparation of ethers of the formula I are 2,4-dinitrochlorobenzene and the corresponding alcohols. For the preparation of 1-(2-methoxyethoxy)-2,4-dinitrobenzene it is known from journal Organic Chemistry USSR 18 (1982), page 1087, to react 2,4-dinitrochlorobenzene with sodium 2-methoxy-ethanolate in 2-methoxyethanol at 90° C. for 4 h. However, the yield which is obtained in this reaction is reported to be only 62%.

For the preparation of 2,4-dinitro-anisole, it is known from Example 23 of German Offenlegungsschrift No. 2,634,419 (corresponding to GB 1,539,183) to react 2,4-dinitrochlorobenzene and methanol in the presence of an aqueous solution of sodium hydroxide and of an aqueous solution of benzyl-dimethyl-lauryl-ammonium chloride as phase-transfer catalyst. The reaction of 2,4-dinitrochlorobenzene with methanol in the presence of sodium hydroxide can also be carried out without the presence of a phase-transfer catalyst at reflux temperature, according to stage 1 of Example 1 of European Pat. No. 0,011,048 (corresponding to U.S. Pat. No. 4,283,536). However, when this process is applied to alcohols of the formula ROH, R having the meaning mentioned in the introduction, some of the desired ethers are obtained only in moderate yields, but in particular it is associated with the occurrence of undesired by-products, especially 2,4-dinitrophenol in amounts of from 7 to 20%.

This makes it absolutely necessary to carry out an elaborate removal of this undesired and interfering by-product because, in the presence of 2,4-dinitrophenol, in the subsequent reaction (for example reduction) of the desired phenol ethers problems, which cannot be overcome industrially, of product quality and reaction control occur, so that a one-pot process, which is desired, cannot be achieved on this basis. Furthermore, the removal and disposal of the 2,4-dinitrophenol takes a form which is, because of its high toxicity, both ecologically and economically expensive.

The process according to the invention for the preparation of 2,4-dinitrophenyl ethers of the general formula I by reaction of a 2,4-dinitrohalogenobenzene of the general formula

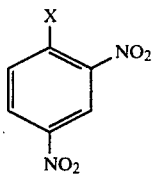 (II)

X denoting —Cl or —Br, with an alkali metal alcoholate of the general formula III

ROM (III)

R having the meaning already mentioned in the introduction, and M denoting an alkali metal cation, in the presence of a solvent, is characterized in that it is carried out at temperatures of —25° C. to —50° C. in a non-polar, inert solvent.

The process according to the invention is preferably carried out at temperatures of —5℗ to —25° C., and very particularly preferably of 0° to +7° C.

Of the compounds of the formula II, 2,4-dinitrochlorobenzene is preferred.

Any desired alkali metal cation such as, for example, $Li^+$, $Na^+$, $K^+$ or $Rb^+$ can represent M, of which $Na^+$ is generally preferred for reasons of cost. The alkali metal alcoholate ROM which is being employed can be used as the substance. However, it can also be prepared in a manner known per se before the actual reaction, in the inert non-polar solvent which is being used, from the alcohol ROH and the alkali metal providing the alkali metal cation M, R and M having the meaning already mentioned.

Normally, this entails the alkali metal being initially introduced into the non-polar, inert solvent which is being used, and being melted and/or finely divided. The alcohol ROH is then metered into this, it also being possible for the alcohol to be dissolved in the non-polar inert solvent. As a rule, the molar ratio between the alkali metal and the alcohol ROH in this is 1:1, but it is also possible to use excesses of alcohol of up to a molar ratio of 1:1.25.

The process according to the invention is carried out in a solvent which, under the reaction conditions, is inert towards the starting materials of the formulae II and III and towards the final product of the formula I and, if the starting material of the formula III is prepared from alkali metal and alcohol ROH, also towards the alkali metal.

Furthermore, the solvents which are used are non-polar, that is to say that, in contrast to, for example, alcohols, esters or nitrites, they have an electric dipole moment which is zero or only low, in the range from 0 to $3.3 \times 10^{-30}$ Cm (Cm=Coulomb×meter; the unit previously used, D=Debye, is obsolete, $3.3 \times 10^{-30}$ Cm are about 0.99 D).

Examples of suitable non-polar inert solvents in this sense are aromatic hydrocarbons such as, for example, benzene, alkylbenzenes such as, for example, toluene, xylenes, ethylbenzene or cycloalkyl-fused aromatics such as, for example, tetralin. It is also possible to use mixtures of two or more of the said solvents. The solvent are advantageously anhydrous when used. The inert, non-polar solvent is used in an amount that is large enough to permit the formation of at least a stirrable suspension of the reaction mixture. To achieve this, approximately 3 to 5 parts by weight of the inert, non-polar solvent is required, relative to 1 part by weight of the 2,4-dinitrohalogenobenzene of the formula II. It is advisable, however, to use this inert, non-polar solvent in an amount that is larger than this minimum amount so that, relative to 1 part by weight of the 2,4-dinitrohalogenobenzene of formula II, appropriately 5 to 150, preferably 5 to 20, parts by weight of the inert, non-polar solvent are employed. It is possible to use the inert, non-polar solvent in an amount that is even larger than that corresponding to the so-called weight ratio of 1:150, but this does not entail any advantages.

The starting components of the formula II and III are mixed in the inert, non-polar solvent or solvent mixture at the said temperatures. As a rule, the molar ratio between the 2,4-dinitro-chlorobenzene or -bromobenzene of the formula II and the alkali metal alcoholate of the formula III in this is 1:(1 to 1.2). Although it is possible to use greater excesses of alkali metal alcoholate, for example up to 11:1.5, this has no advantages. Normally, the two starting components of the formula II and III are initially dissolved or suspended in the solvent or solvent mixture and then slowly mixed. As a rule, this entails the solution of the compound of the formula II being initially introduced and, while mixing, the suspension of the alkali metal alcoholate of the formula III being metered in.

In certain circumstances, the suspension of the alkali metal alcoholate can be converted into a solution by a temperature increase, and thus more readily metered uniformly. However, in this case particular care has to be taken that the said reaction temperatures are not exceeded.

The alkoxy and alkyl groups in the radicals representing R can be straight-chain or branched. The alkali metal alcoholates of the formula III can be derived from, for example, the following alcohols:

methylglycol (=ethylene glycol monomethyl ether, the following designations being formed analogously), ethylglycol, propylglycol, isopropylglycol, butylglycol, phenylglycol; methyldiglycol (=diethylene glycol monomethyl ether, the following designations being formed analogously), ethyldiglycol, isopropyldiglycol, butyldiglycol, isobutyldiglycol; 2- or 3-methoxypropanol, 2- or 3-propoxypropanol, 2- or 3-isopropoxypropanol, 2- or 3-isobutoxypropanol, 2-, 3- or 4-methoxybutanol, 2-, 3- or 4-isopropoxybutanol, 2-, 3- or 4-butoxybutanol, 2-, 3- or 4-isobutoxybutanol; 4,8-dioxa-1-nonanol, 4,8-dioxa-1-decanol, 4,8-dioxa-1-undecanol, 5,10-dioxa-1-undecanol, 5,10-dioxa-1-dodecanol, 3,6-dioxa-2,5-dimethyl-1-heptanol, 3,6-dioxa-2,5-dimethyl-1-nonanol, 3,6-dioxa-2,5-diethyl-1-octanol, and tetrahydrofurfuryl alcohol.

The alcoholate of the formula III is preferably derived from methylglycol (ethylene glycol monomethyl ether), that is to say an alkali metal 2-methoxyethanolate is preferably used for the compound III.

When a mixture having two or more different radicals R is used as the alkali metal alcoholate of the formula III, R having the meaning mentioned in the introduction, then mixtures of two or more compounds of the formula I are produced.

The reaction mixture resulting after completion of the reaction can, after an excess of alcoholate has been destroyed where appropriate, and after removal of the precipitated alkali metal salts, either be used without intermediate isolation for subsequent reactions, for example for catalytic reduction, or be worked up by processes known per se.

Any excess of remaining alkali metal alcoholate which is present is destroyed by addition of an equivalent amount of an inorganic or organic acid such as, for example, sulphuric acid, acetic acid, oxalic acid or benzoic acid. After extraction by stirring with water and phase separation, the 2,4-dinitrophenyl ether of the formula I can be isolated by removal of the solvent by distillation, where appropriate under reduced pressure.

High yields of ethers of the formula I, which are 97% or more, are obtained in the process according to the invention. The contents of by-products, in particular of 2,4-dinitrophenol, are below 2% and they decrease to negligible figures below 0.3% (dinitrophenol below 0.1%) when the reaction is carried out at temperatures below $-25°$ C. The increase in yield and drastic reduction in the formation of by-products could not have been foreseen, especially their extents, since a greater occurrence of by-products, such as, for example, of azoxy and azo compounds, was to be feared in reactions of 2,4-dinitrohalogenobenzenes with alcoholates in non-polar organic solvents.

Compared with a reaction of alkali metal alcoholates with 2,4-dinitrohalogenobenzene in the presence of a polar organic solvent, such as, for example, in a straight-chain or branched alcohol, for example methanol or ethanol, or in a straight-chain or branched alkyl acetate or in a glycol or glycol ether, the use on non-polar organic solvents in the process according to the invention offers, for example, the advantage that in the preparation of the alcoholate from the alkali metal and the alcohol on the large industrial scale the feeding of the former can take a considerably simpler form, and the reaction can be kept under control considerably more easily. In addition, it is possible completely to prevent decomposition of the alkali metal alcoholate. Furthermore, the use of a non-polar solvent which is immiscible with water offers advantages in the working up of the reaction mixture and in subsequent reactions without intermediate isolation of the product.

In the examples which follow, temperatures are stated in degrees Celsius. Unless otherwise indicated, parts denote parts by weight and percentages denote percentages by weight.

EXAMPLE 1

β-Methoxyethoxy-2,4-dinitrobenzene 24.2 g of sodium are melted in 1,000 ml of xylene. At 100° C., 83.6 g of methylglycol (=ethylene glycol monomethyl ether) are added dropwise, and the mixture is stirred until the sodium has completely dissolved. The suspension is cooled and added, within 2 h, at 0° to 5° C. to a solution of 202.6 g of 2,4-dinitrochlorobenzene in 400 ml of xylene. The mixture is then stirred for a further 60 min.

Then, to destroy the excess of base, 2.5 g of $H_2SO_4$ are added, and the precipitated salts (sodium chloride and sodium sulphate) are removed.

The solution of β-methoxyethoxy-2,4-dinitrobenzene thus obtained can be used directly for further reactions.

To isolate the compound, 2.5 g of $H_2SO_4$ and 500 ml of warm water (50°) are added to the reaction solution. After extraction by stirring and phase separation, the solvent is removed from the organic phase under water pump vacuum.

257.9 g of β-methoxyethoxy-2,4-dinitrobenzene (98.3% of theory based on 2,4-dinitrochlorobenzene) are obtained as a yellow crystalline solid of melting point 36° C. The purity determined by gas chromatography is above 99%.

EXAMPLE 2

(Comparison Example)

In analogy to reaction step 1 of European Pat. No. 0,011,048, 213 g of molten 2,4-dinitrobenzene are introduced into 632 g of methylglycol and dissolved by stirring. 86 g of 50% strength aqueous NaOH solution are added dropwise to the stirred solution at 65° C. The mixture is then stirred at 65° C. for one hour.

The resulting reaction mixture contains, according to HPLC analysis, β-methoxyethoxy-2,4-dinitrobenzene and 2,4-dinitrophenol in the ratio by weight of 73:21, together with 6 parts of by-products which were not specifically identified. 800 g of ice are added to the mixture, and the precipitated product is filtered off with suction and washed with 2 L of cold water. 193 g (75% of theory) of a dark-brown oil containing byproducts (purity determined by gas chromatography 94%) are obtained. 36.7 g (19%) of 2,4-dinitrophenol are obtained from the aqueous phase by acidification to pH 1.

EXAMPLE 3

(Comparison Example)

In a repetition of Example 2, 42 g of solid NaOH are used in place of aqueous NaOH solution.

229.2 g (=90.2% of theory) of β-methoxyethoxy-2,4-dinitrobenzene are obtained as a dark-brown solid of melting point: 31° to 33° C., which has a purity of 97% determined by gas chromatography. 13.5 g (7%) of 2,4-dinitrophenol are isolated from the aqueous phase by acidification to pH 1.

EXAMPLE 4

In a repetition of Example 1, 152 g of phenylglycol are used in place of methylglycol.

298.1 g (=98% of theory) of β-phenoxyethoxy-2,4-dinitrobenzene, of melting point: 61° to 62° C. and with a purity of 99.8% determined by gas chromatography, are obtained.

EXAMPLE 5

In a repetition of Example 1, 132.2 g of methyldiglycol (=diethylene glycol monomethyl ether) are used in place of the methylglycol.

278.1 g (=97.2% of theory) of 2-(2-methoxyethoxy)ethoxy-2,4-dinitrobenzene, of melting point: 43° to 45° C. and with a purity of 99.8% determined by gas chromatography, are obtained.

EXAMPLE 6

In a repetition of Example 1, 114.6 g of 3-methoxybutanol are used in place of the methylglycol.

262 g (=97% of theory) of (3-methoxybutoxy)-2,4-dinitrobenzene of melting point: 42° to 43° C. and with a purity of 99.7% determined by gas chromatography, are obtained.

EXAMPLE 7

In a repetition of Example 1, 112 g of tetrahydrofurfuryl alcohol are used in place of the methylglycol.

260 g (=97% of theory) of (tetrahydrofurfuryloxy)-2,4-dinitrobenzene, of melting point: 52° to 54° C. and with a purity of 99.8% determined by gas chromatography, are obtained.

EXAMPLES 8 to 12

Methylglycol (=ethylene glycol monomethyl ether) and 2,4-dinitrochlorobenzene are reacted in a manner analogous to that in Example 1. The table which follows indicates the alkali metal M which is used, the molar ratio alkali metal:methylglycol: 2,4-dinitrochlorobenzene, the solvent, the reaction temperature and the reaction time. The yields of β-methoxyethoxy-2,4-dinitrobenzene indicated in the table are obtained by this. The melting point and purity of the products correspond to that of the material obtained by Example 1.

TABLE

| No. | M | Molar ratio | Solvent | Reaction temp. in °C. | Reaction time in h | Yield in % |
|-----|-----|-------------|----------|----------------------|--------------------|------------|
| 8 | Li | 1.1:1.15:1 | Xylene | 0–5 | 3 | 98.6 |
| 9 | K | 1.1:1.15:1 | Xylene | 0–5 | 3 | 98.0 |
| 10 | Na | 1.2:1.3:1 | Toluene | 40 | 2 | 97.8 |
| 11 | Na | 1.2:1.5:1 | Toluene | −20 | 5 | 98.1 |
| 12 | Na | 1.0:1.1:1 | Ethylbenzene | 25 | 3 | 98.2 |

What is claimed is:

1. In the improved process for the preparation of 2,4-dinitrophenyl ethers of the formula

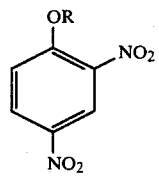

wherein R is $(C_1-C_4)$alkoxy-$(C_2-C_4)$alkyl, phenoxy-$(C_2-C_4)$alkyl, $(C_1-C_4)$alkoxy-$(C_2-C_4)$alkoxy-$(C_2-C_4)$alkyl or tetrahydrofurfuryl, wherein 2,4-dinitrohalobenzene of the formula

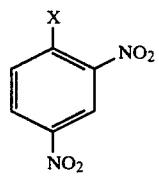

is reacted with an alkali metal alcoholate of the formula

ROM wherein X is —Cl or —Br and M is an alkali metal cation,
the improvement comprises reacting the dinitrohalobenzene and alkali metal alcoholate at a temperature of −25° C. to 50° C. in a non-polar, inert solvent.

2. The process according to claim 1 wherein the molar ratio of 2,4-dinitrohalobenzene:alkali metal alcoholate is 1:(1 to 1.2).

3. The process according to claim 1 wherein the reaction temperature is from −5° to 25° C.

4. The process according to claim 3 wherein the reaction temperature is from 0° to 7° C.

5. The process according to claim 1 wherein a solution of 2,4-dinitrohalobenzene is mixed with a solution or suspension of the alkali metal alcoholate.

6. The process according to claim 1 wherein a solution of the 2,4-dinitrohalobenzene of the formula II is initially introduced into a reaction vessel and then a solution or suspension of the alkali metal alcoholate is added.

7. The process according to claim 1 wherein 2,4-dinitrohalobenzene is 2,4-dinitrochlorobenzene.

8. The process according to claim 1 wherein the alkali metal alcoholate is alkali metal 2-methoxyethanolate.

9. The process according to claim 1 wherein the alkali metal alcoholate is sodium alcoholate.

10. The process according to claim 1 wherein the inert solvent is a solvent which has a dipole moment from 0 to $3.3 \times 10^{-30}$ Cm.

11. The process according to claim 1 wherein the inert solvent is benzene, toluene, xylene, ethylbenzene, tetralin or mixtures thereof.

12. An improved process for preparation of 2,4-dinitrophenyl ethers which comprises reacting a 2,4-dinitrohalobenzene with 2-methoxy-ethanolate at $-25°$ to $50°$ C. in the presence of a non-polar, inert solvent.

* * * * *

UNITED STATES PATENT AND TRADEMARK OFFICE
CERTIFICATE OF CORRECTION

PATENT NO. : 4,695,656
DATED : September 22, 1987
INVENTOR(S) : Kuno Reh

It is certified that error appears in the above-identified patent and that said Letters Patent is hereby corrected as shown below:

Column 1, line 28, change "journal" to read --Journal--;

Column 2, line 21, change "-5® to +25°C.," to read -- -5 to +25°C.,--;

Column 3, line 19, change "11 : 1.5" to read --1 : 1.5--;

Column 2, line 18, change "-50°C" to read -- +50°C--.

Signed and Sealed this

Tenth Day of May, 1988

Attest:

DONALD J. QUIGG

Attesting Officer

Commissioner of Patents and Trademarks